(12) United States Patent
Arocha

(10) Patent No.: US 10,420,888 B2
(45) Date of Patent: Sep. 24, 2019

(54) DOUBLE-CHAMBER MIXING SYRINGE AND METHOD OF USE

(71) Applicant: Max Arocha, Plantation, FL (US)

(72) Inventor: Max Arocha, Plantation, FL (US)

( * ) Notice: Subject to any disclaimer, the term of this patent is extended or adjusted under 35 U.S.C. 154(b) by 578 days.

(21) Appl. No.: 14/475,764

(22) Filed: Sep. 3, 2014

(65) Prior Publication Data

US 2015/0065993 A1 Mar. 5, 2015

Related U.S. Application Data

(60) Provisional application No. 61/872,963, filed on Sep. 3, 2013.

(51) Int. Cl.
*A61M 5/19* (2006.01)
*A61M 5/24* (2006.01)
*A61M 5/315* (2006.01)

(52) U.S. Cl.
CPC ............ *A61M 5/19* (2013.01); *A61M 5/2466* (2013.01); *A61M 5/31551* (2013.01); *A61M 5/31563* (2013.01); *A61M 5/3158* (2013.01); *A61M 2205/583* (2013.01)

(58) Field of Classification Search
CPC ...... A61M 5/28; A61M 1/0068; A61M 25/09; A61M 25/003; A61M 25/00; A61M 25/098
See application file for complete search history.

(56) References Cited

U.S. PATENT DOCUMENTS

| | | | | |
|---|---|---|---|---|
| 3,373,906 A | * | 3/1968 | De Hart | A61M 3/005 222/235 |
| 3,470,869 A | * | 10/1969 | Fenton | A61K 49/04 600/435 |
| 3,587,982 A | * | 6/1971 | Campbell | B01F 13/002 222/129 |
| 3,738,535 A | * | 6/1973 | Nicholls | A61M 5/31596 222/137 |
| 3,774,604 A | * | 11/1973 | Danielsson | A61M 39/0606 137/625.47 |
| 3,815,878 A | * | 6/1974 | Baskas | A61C 9/0026 206/219 |
| 3,953,002 A | * | 4/1976 | England, Jr. | B01F 3/10 261/76 |
| 4,040,420 A | * | 8/1977 | Speer | A61M 5/19 604/191 |
| 4,044,757 A | * | 8/1977 | McWhorter | A61M 3/0262 600/432 |
| 4,069,814 A | * | 1/1978 | Clemens | A61M 1/0084 600/581 |

(Continued)

FOREIGN PATENT DOCUMENTS

WO PCT/US2010/041613 A1 1/2011
WO WO 2013/126173 A1 8/2013

OTHER PUBLICATIONS

International Search Report in PCT/US2014/053797, dated Mar. 31, 2015.

*Primary Examiner* — Bhisma Mehta
*Assistant Examiner* — Matthew A Engel
(74) *Attorney, Agent, or Firm* — Ted Whitlock

(57) ABSTRACT

Described is a syringe housing at least one removable carpule containing at least two injectable solutions and having a mixing chamber for mixing two injectable solutions during administration of the solutions, and methods of using the syringe.

2 Claims, 5 Drawing Sheets

(56) References Cited

U.S. PATENT DOCUMENTS

| | | | | |
|---|---|---|---|---|
| 4,265,618 A * | 5/1981 | Herskovitz | A61C 5/04 | 219/230 |
| 4,275,729 A | 6/1981 | Silveer et al. | | |
| 4,538,920 A * | 9/1985 | Drake | A61C 5/064 | 222/137 |
| 4,631,055 A * | 12/1986 | Redl | A61B 17/00491 | 222/135 |
| 4,673,395 A * | 6/1987 | Phillips | A61M 5/19 | 604/191 |
| 4,689,042 A * | 8/1987 | Sarnoff | A61M 5/2066 | 604/136 |
| 4,753,536 A * | 6/1988 | Spehar | A61C 5/062 | 222/137 |
| 4,795,433 A * | 1/1989 | Sarnoff | A61K 9/0019 | 604/134 |
| 4,808,184 A * | 2/1989 | Tepic | A61L 24/06 | 215/DIG. 8 |
| 4,874,368 A * | 10/1989 | Miller | A61B 17/00491 | 222/137 |
| 4,978,336 A * | 12/1990 | Capozzi | A61B 17/00491 | 222/137 |
| 5,015,232 A * | 5/1991 | Maglinte | A61M 1/0084 | 604/102.02 |
| 5,104,375 A * | 4/1992 | Wolf | A61B 17/00491 | 206/364 |
| 5,116,315 A * | 5/1992 | Capozzi | A61B 17/00491 | 222/137 |
| 5,147,323 A * | 9/1992 | Haber | A61M 5/19 | 604/191 |
| 5,174,653 A * | 12/1992 | Halat | B01F 5/0615 | 138/37 |
| 5,188,602 A * | 2/1993 | Nichols | A61F 7/123 | 604/107 |
| 5,199,949 A * | 4/1993 | Haber | A61M 5/19 | 604/191 |
| 5,211,627 A * | 5/1993 | William | A61M 25/003 | 604/523 |
| 5,240,146 A * | 8/1993 | Smedley | A61M 5/19 | 222/137 |
| 5,271,527 A * | 12/1993 | Haber | A61M 5/19 | 222/137 |
| 5,298,023 A * | 3/1994 | Haber | A61M 5/2448 | 604/191 |
| 5,306,237 A * | 4/1994 | Clement | A61B 10/04 | 604/30 |
| 5,314,412 A * | 5/1994 | Rex | A61M 5/19 | 222/137 |
| 5,443,454 A * | 8/1995 | Tanabe | A61B 17/12022 | 604/264 |
| 5,445,614 A * | 8/1995 | Haber | A61M 5/19 | 604/191 |
| 5,472,422 A * | 12/1995 | Ljungquist | A61M 5/2448 | 604/518 |
| 5,474,540 A * | 12/1995 | Miller | A61M 25/0026 | 604/191 |
| 5,478,323 A * | 12/1995 | Westwood | A61M 5/19 | 604/191 |
| 5,505,704 A * | 4/1996 | Pawelka | A61M 5/19 | 604/191 |
| 5,542,934 A | 8/1996 | Silver | | |
| 5,575,409 A * | 11/1996 | Gruendeman | B05C 17/00513 | 222/459 |
| 5,584,815 A * | 12/1996 | Pawelka | A61M 5/19 | 604/135 |
| 5,685,846 A * | 11/1997 | Michaels, Jr. | A61M 5/31596 | 604/181 |
| 5,725,498 A * | 3/1998 | Janzen | A61B 17/0057 | 128/898 |
| 5,749,968 A * | 5/1998 | Melanson | A61K 38/42 | 118/300 |
| 5,814,022 A * | 9/1998 | Antanavich | A61B 17/00491 | 604/181 |
| 5,865,818 A * | 2/1999 | Gould | A61M 5/178 | 604/187 |
| 5,935,437 A * | 8/1999 | Whitmore | A61M 1/3496 | 206/438 |
| 6,033,401 A * | 3/2000 | Edwards | A61B 17/00491 | 606/214 |
| 6,053,899 A * | 4/2000 | Slanda | A61B 17/0483 | 604/500 |
| 6,371,975 B2 * | 4/2002 | Cruise | A61B 17/00491 | 606/214 |
| 6,454,739 B1 * | 9/2002 | Chang | A61B 17/00491 | 239/399 |
| 6,471,670 B1 * | 10/2002 | Enrenfels | A61B 17/00491 | 604/191 |
| 6,547,101 B1 | 4/2003 | Sogaro | | |
| 6,599,008 B2 * | 7/2003 | Heusser | B01F 3/10 | 366/337 |
| 6,612,465 B2 | 9/2003 | Pierson et al. | | |
| 6,629,774 B1 * | 10/2003 | Gruendeman | B05C 17/002 | 222/145.6 |
| 6,629,947 B1 * | 10/2003 | Sahatjian | A61B 17/12022 | 604/11 |
| 6,648,852 B2 * | 11/2003 | Wirt | A61B 17/00491 | 604/191 |
| 6,699,214 B2 * | 3/2004 | Gellman | A61M 5/2066 | 604/187 |
| 6,796,966 B2 * | 9/2004 | Thomas | A61K 31/00 | 222/386 |
| 6,972,005 B2 * | 12/2005 | Boehm, Jr. | A61B 17/00491 | 222/135 |
| 6,994,686 B2 * | 2/2006 | Cruise | A61B 17/00491 | 604/104 |
| 7,018,089 B2 | 3/2006 | Wenz et al. | | |
| 7,037,289 B2 * | 5/2006 | Dodge | A61B 17/00491 | 604/191 |
| 7,270,654 B2 * | 9/2007 | Griego | A61M 25/0026 | 604/518 |
| 7,575,131 B2 * | 8/2009 | Feinberg | A61B 17/00491 | 222/1 |
| 7,811,291 B2 * | 10/2010 | Liu | A61B 17/8811 | 604/82 |
| 7,850,656 B2 * | 12/2010 | McKay | A61B 17/3478 | 604/173 |
| 7,914,484 B2 * | 3/2011 | Yokoyama | A61B 17/00491 | 604/83 |
| 7,955,301 B1 * | 6/2011 | McKay | A61M 5/488 | 137/517 |
| 7,985,020 B2 * | 7/2011 | Pappalardo | B01F 5/0641 | 366/337 |
| 8,047,407 B2 * | 11/2011 | Wheeler | A61B 17/00491 | 222/255 |
| 8,221,452 B2 * | 7/2012 | Edwards | A61B 17/00491 | 604/82 |
| 8,308,681 B2 * | 11/2012 | Slocum | A61B 17/00491 | 604/82 |
| 8,353,866 B2 | 1/2013 | Evans, Jr. | | |
| 8,425,463 B2 | 4/2013 | Patrick | | |
| 2001/0047187 A1 * | 11/2001 | Milo | A61B 17/0057 | 606/213 |
| 2002/0052579 A1 | 5/2002 | Sogaro | | |
| 2003/0048694 A1 * | 3/2003 | Horner | B01F 5/0617 | 366/337 |
| 2003/0055454 A1 * | 3/2003 | Zucker | A61B 17/0057 | 606/213 |
| 2006/0208000 A1 * | 9/2006 | Murray | B29B 7/7404 | 222/135 |
| 2007/0073267 A1 * | 3/2007 | Muller | A61M 5/1408 | 604/506 |
| 2007/0088271 A1 * | 4/2007 | Richards | A61M 5/14244 | 604/151 |
| 2007/0164047 A1 * | 7/2007 | Reidt | A61C 5/064 | 222/137 |
| 2007/0191781 A1 * | 8/2007 | Richards | A61B 17/00491 | 604/191 |
| 2007/0213686 A1 * | 9/2007 | Mathur | A61M 5/1723 | 604/518 |

(56) References Cited

U.S. PATENT DOCUMENTS

| | | | | |
|---|---|---|---|---|
| 2008/0045925 A1* | 2/2008 | Stepovich | A61M 5/14566 | 604/518 |
| 2008/0103564 A1* | 5/2008 | Burkinshaw | A61B 17/00491 | 607/96 |
| 2008/0121657 A1* | 5/2008 | Voegele | B05C 17/00553 | 222/137 |
| 2008/0125798 A1* | 5/2008 | Osborne | A61B 17/221 | 606/159 |
| 2008/0260598 A1* | 10/2008 | Gross | A61F 2/4644 | 422/162 |
| 2008/0262469 A1* | 10/2008 | Brister | A61B 5/0002 | 604/504 |
| 2009/0099547 A1* | 4/2009 | Radmer | A61J 1/2089 | 604/519 |
| 2009/0122638 A1* | 5/2009 | Sato | B01F 3/0861 | 366/339 |
| 2009/0124986 A1* | 5/2009 | Hayakawa | B01F 5/0262 | 604/290 |
| 2009/0131864 A1* | 5/2009 | Pickhard | A61M 5/284 | 604/83 |
| 2009/0149746 A1* | 6/2009 | Chernomorsky | A61B 90/39 | 600/433 |
| 2009/0170933 A1* | 7/2009 | Leckrone | A61K 31/21 | 514/502 |
| 2009/0198217 A1* | 8/2009 | Thorne, Jr. | A61J 1/2096 | 604/518 |
| 2009/0306623 A1* | 12/2009 | McIntosh | A61B 17/00491 | 604/506 |
| 2009/0318893 A1* | 12/2009 | English | A61J 1/2089 | 604/520 |
| 2010/0010436 A1* | 1/2010 | Wang | B65D 81/325 | 604/89 |
| 2010/0054075 A1* | 3/2010 | Valaie | A61B 17/8819 | 366/6 |
| 2010/0063440 A1* | 3/2010 | Kitani | A61M 39/045 | 604/83 |
| 2010/0145304 A1* | 6/2010 | Cressman | A61B 18/06 | 604/506 |
| 2010/0217231 A1* | 8/2010 | Ilan | A61B 17/00491 | 604/506 |
| 2010/0268158 A1* | 10/2010 | Porter | A61B 17/00491 | 604/82 |
| 2011/0106071 A1* | 5/2011 | Bosel | A61B 18/06 | 606/28 |
| 2011/0128814 A1* | 6/2011 | Hanada | B01F 5/0614 | 366/339 |
| 2011/0150703 A1* | 6/2011 | Castro | B01F 5/061 | 422/68.1 |
| 2011/0152616 A1* | 6/2011 | Deal | A61B 1/00089 | 600/114 |
| 2011/0184350 A1* | 7/2011 | McKay | A61B 17/3401 | 604/174 |
| 2011/0245803 A1* | 10/2011 | Barker, Jr. | A61B 17/00491 | 604/518 |
| 2011/0251546 A1* | 10/2011 | Sullivan | A61M 15/0028 | 604/22 |
| 2011/0275988 A1* | 11/2011 | Davis | A61M 5/1411 | 604/82 |
| 2011/0276031 A1* | 11/2011 | Hoang | A61M 5/1411 | 604/518 |
| 2011/0288531 A1* | 11/2011 | Chang | A61M 5/31596 | 604/518 |
| 2011/0295212 A1* | 12/2011 | Greter | A61B 17/00491 | 604/191 |
| 2011/0301545 A1* | 12/2011 | Nalesso | A61M 5/19 | 604/191 |
| 2012/0029471 A1* | 2/2012 | Lee | A61M 5/19 | 604/518 |
| 2015/0065993 A1* | 3/2015 | Arocha | A61M 5/19 | 604/506 |

\* cited by examiner

DOUBLE-CHAMBER MIXING SYRINGE AND METHOD OF USE

CROSS-REFERENCE TO RELATED APPLICATIONS

This application is a non-provisional application claiming priority to or the benefit of U.S. Provisional Patent Application, Ser. No. 61/872,963, filed Sep. 3, 2013.

BACKGROUND OF THE INVENTION

Local anesthetics are the safest and most effective drugs in medicine for the prevention and management of pain.

Effectiveness of a local anesthetic is assessed by its "onset time" and duration. Onset time, also referred to as "latency time," is the period of time between administration and its blocking effect on sensory and motor nerve sensation (numbing effect.)

For more than 100 years, buffering/alkalinization of local anesthetics has been reported in the scientific literature for improving onset time and making the injection of a local anesthetics more comfortable and less painful. The term "anesthetics buffering", "alkalinization" and "pH buffering" are medical terms used for optimizing the pH of local anesthetics before injection.

Solutions containing bicarbonate ions are routinely used to buffer the pH of local anesthetics, which are typically acidic, and other parenteral solutions. A commonly used medical bicarbonate solutions is sodium bicarbonate ($NaHCO_3$) mixed with water.

Mixing syringes capable of mixing two fluids within a syringe barrel and delivery of same from a single port for administration/injection have been described. However, the vast majority of these known mixing syringes provide separate chambers for each fluid whereby the chambers are axially aligned, i.e., are "stacked" one on top of the other within the syringe barrel. U.S. Pat. No. 8,353,866 describes a dual-chambered syringe wherein the chambers are configured parallel to one another, or "side-by-side," within the syringe barrel, for mixing two fluids prior to administration, but this device provides a divided, open lumen for containing the fluids and is not configured to receive a prefabricated carpule of drug and diluent.

Despite the long history of anesthetic buffering, technological advances have failed to make buffering of local anesthetics practical, efficient, or easy-to-use in a clinical setting. Commercially available devices for dispensing buffered local anesthetics involve a high degree of technique and require health care professionals to manually mix the bicarbonate with the anesthetic, on-site, prior to filling of the syringe for administration of the buffered anesthetic.

Prior local anesthetic syringe devices did not control the pH in which the local anesthetic solution exits the syringe device.

Among these deficiencies, conventional methods and devices still have the following disadvantages:
1. The on-site preparation time is greater than the actual time require to administer the same.
2. The buffered anesthetic solution is prepared in bulk, in amounts greater than initially administered, in order to provide for subsequent administrations, if needed; the pH of buffered anesthetic solution can decrease, and activity can diminish, over relatively short time periods.
3. Freshly mixing buffered anesthetic solutions for subsequent administrations require preparation steps (e.g., mixing) to be repeated.

It is therefore an object of this invention to provide a novel dispensing device and method which can overcome these known disadvantages and deficiencies.

SUMMARY OF THE INVENTION

The subject invention concerns a syringe, system and method for dispensing a mixture of drug and a diluent buffer or second drug composition or solution.

For purposes of the subject invention, the terms "distal" or "superior" and "proximal" and "inferior" are used to describe the relative position of the components of the syringe or system. "Distal" or "superior" refers to the end farthest away from the patient when the syringe is used, i.e., the end from which the user of the syringe activates the plunger; "proximal" or "inferior" refers to the end closest to the patient when in use, i.e., the end of the syringe engaged with a hypodermic needle.

A syringe of the invention comprises:

a syringe plunger slidingly engaging with a syringe barrel, said plunger comprising at least two plunger stems, each stem, at its proximal end, engaging, from a single depression or actuation of the plunger, a distal end of at least two carpule chambers containing an injectable fluid. The carpule chambers can be formed in a single, multi-chambered carpule or formed separately in more than one (typically two) individual carpules. The carpules can be provided separately or adjoined to one another;

a syringe housing forming the body or barrel of the syringe, said housing capable of receiving at least one multi-chambered carpule or at least two single-chambered carpules, the carpule chambers respectively containing an injectable drug composition, such as a solution or suspension of local anesthetic, and at least one other or second injectable fluid, such as a buffer or diluent, e.g., an aqueous sodium bicarbonate solution, or a second drug composition.

a carpule-piercing means for engaging with and opening or piercing through a capped or sealed proximal end of the one or more carpules when the piercing means and carpule engage one another following application of pressure via the plunger, said carpule-piercing means being distal to:

a mixing chamber in communication with the carpule-piercing means for receiving and adequately mixing the fluids dispensed from the pierced carpule chambers, prior to or during administration of the mixture, and an exit port or nozzle at a proximal end of the syringe, opposite the plunger end, for dispensing the mixed injectable drug and second injectable fluid from the mixing chamber, whereby:

depressing or actuating the plunger causes piercing of the carpule or a cap or sealed end of the carpule, to deliver a predetermined amount or volume of drug and second injectable fluid to be thoroughly mixed in the mixing chamber before being administered through the exit port or nozzle.

It would be understood that the exit port or nozzle can be configured, as in a conventional syringe, to receive a disposable hypodermic needle for injection of the mixed drug/buffer composition into the tissue of a patient in need of the drug composition.

As part of the invention, the system further includes a double barrel carpule. One barrel of the carpule contains commercially available anesthetic solution and the other contains a commercially available sodium bicarbonate solution or a second drug composition.

A syringe of the invention comprises a double plunger by which the anesthetic and sodium bicarbonate solutions are simultaneously discharged into a common mixing chamber in calibrated proportions (example 8:1) as the mixed solution is administered to the targeted tissue from the end of the mixing chamber via a needle affixed at the other end of the mixing chamber. The needle, mixing chamber assembly and the carpule assembly can be configured to be readily removable from the body of the syringe.

The subject invention further comprises a method of administering a mixture of two injectable fluids by employing a novel syringe as described and shown herein.

An advantage of the present invention is convenience of use and greater efficiency in a clinical setting for injectable drugs, such as anesthetics, which are commonly mixed with another solution immediately prior to administration. This advantage is achieved by providing a dispensing device in accordance with the subject invention comprising a syringe barrel adapted to receive at least one double-chambered carpule containing in each respective chamber a first drug composition and a second fluid composition, such as a buffer or diluent to be mixed with the drug composition. It would be understood that the syringe barrel configuration can also receive at least two conventional, single-chambered carpules as currently available in the commercial market.

The subject syringe further comprises a carpule-piercing means and fluid communication between the carpule and a mixing chamber constructed and arranged to receive predetermined amounts or volumes of each fluid and instantly mix those compositions immediately prior to administration to a target tissue.

Accordingly, it is an object of the present invention to provide a mixing syringe which is inexpensive to manufacture, reusable, capable of being sterilized, and efficient in operation.

Another object of the present invention is to provide a mixing syringe which will deliver freshly mixed anesthetic and buffer solution, without pre-mixing or repeated mixing steps for subsequent administrations of anesthetic.

Another object of the present invention is to provide a mixing syringe which provides accurately measured and adequately mixed fluids from two pre-filled (pre-measured) carpule chambers for administration at calibrated increments of the resulting mixture at a manually controlled rate.

Another object of the present invention is to provide a mixing syringe which will reduce waste of buffered drug solution and increase efficiency by reducing the time and effort expended by a health care professional to pre-mix commercial anesthetic and buffer solutions prior to administering the same.

Another object of the invention is to provide a mixing syringe which will provide freshly mixed solutions in variable amounts and preventing decrease of pH of the solution over time when multiple, staggered injections are required during a lengthy medical procedure.

Another object of the present invention is to provide a mixing syringe in which a double-chamber carpule may be readily and easily inserted into the syringe barrel and in which the needle nozzle assembly therefore may be readily and easily changed and rotated 360° as desired.

Another object of the present invention is to provide a method of mixing buffered local anesthetic solution which will obviate the necessity of on-site mixing devices and methods.

Another object of the present invention is to provide a disposable double-chamber carpule which may be readily and easily inserted into a syringe body adapted for receiving such double-chamber carpule and use thereof, and which can be readily and easily removed therefrom after use, thereby requiring no additional operational or pre-mixing steps as compared to the use of a conventional syringe.

Another object of the present invention is to provide a mixing syringe which permits the mixing of calibrated amounts of two solutions contained within juxtaposed barrels or barrel chambers, enabling the mixed solution to be administered directly from the mixing zone into the target tissue of a patient.

Another object of the present invention is to provide a syringe device that can be adjusted and calibrated to administer local anesthetics at, or near, physiological pH by controlling the pH in which the solution exits the mixing chamber from the syringe device.

These objects or advantages of the subject device and method, as well as other embodiments, objects or advantages not expressly provided, would be apparent and readily understood by the description and drawings provided herein.

DETAILED DESCRIPTION OF THE INVENTION

Figure 1:
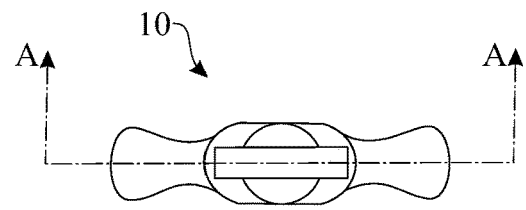
FIG. 1 is a top view of an embodiment of a syringe device in accordance with the subject invention, illustrating the line of cross-section, A-A, by which all views are referenced in FIGS. 2-6.

The subject invention concerns a syringe and method of using the syringe which can provide for mixing, immediately prior to use, at least two separately contained fluids, and delivering the mixture to a target in a single actuation of a syringe plunger. The syringe of the invention comprises:

a dual-stemmed syringe plunger, a syringe housing forming the body or barrel of the syringe, capable of receiving at least one carpule containing an injectable drug composition, a carpule-piercing means, a mixing chamber in communication with the carpule-piercing means, and an exit port or nozzle at one end of the syringe, opposite the plunger end.

It would be understood that the exit port or nozzle can be configured, as in a conventional syringe, to receive a hypodermic needle, such as a disposable hypodermic needle.

The dual-stemmed plunger of the subject syringe is slidingly engaged with the syringe barrel. Each stem of the plunger can have a fixed length, or an adjustable length. A preferred embodiment includes a dual-stemmed plunger where one stem has a fixed length, and the other stem has an adjustable length. Advantageously, the dual-stemmed plunger engages, from a single depression or actuation, two carpule plugs provided in corresponding carpule chambers. The two or more carpule chambers can be formed in individual carpules or from a single, multi-chambered carpule, wherein each chamber of the carpule or carpules contains an injectable fluid.

A carpule is well known in the medical field as a type of ampule or cartridge containing a liquid medicament to be administered, typically by injection using a hypodermic needle and syringe. Typically, a carpule is a metal or glass tube or cylinder with a puncturable cap or seal on one end and a sliding plug on the other end.

The sliding plug of the carpule can push the contained fluid from the opposite, punctured end when depressed by a syringe plunger. The dual-stemmed syringe plunger of the subject invention can engage a single, multi-chambered carpule or more than one individual carpule. Preferably, each carpule plug is formed from a material, such as rubber, polymer, or the like and can be configured having a thickness so that a sharp or pointed end of the plunger stem can penetrate into the material to facilitate its engagement, but without completely puncturing the plug so that fluid contained within the carpule does not leak through the plug.

For purposes of the subject invention, the syringe is described for use for injecting a buffered anesthetic, and more preferably, a local anesthetic buffered with an aqueous sodium bicarbonate solution. It would be understood that the device and methods described herein are not limited to administration of local anesthetics, but can be adapted for use with any medication requiring dilution with a diluent, buffering with a buffer, or mixing with another medication, prior to administration.

Local anesthetics are commonly pre-mixed with a buffer, such as an aqueous salt solution, prior to injection or administration, to lessen pain (e.g., "stinging") experienced by a patient during administration, to decrease onset time (faster onset), and to increase duration of activity of the anesthetic. Thus, carpules used in carrying out a process of the subject invention can contain a solution or suspension of local anesthetic, or a buffer or diluent, such as an aqueous sodium bicarbonate solution.

It would be recognized that each solution can be contained within separate, individual carpules, or both solutions can be contained within a single carpule having a divided chamber or lumen for separately holding at least two solutions, for use with the subject invention. Typically, a carpule or carpule chamber containing a local anesthetic solution, and a second carpule or carpule chamber containing a buffer solution are employed.

In order to mix the separate solutions, a carpule-piercing or puncturing means is provided for engaging with and piercing or puncturing the cap end of the carpule. The plunger can then apply pressure to the sliding plug end of the carpule, forcing the solutions out of the carpule. Preferably, the carpule-piercing means is a hollow needle which is in communication with the contents of the carpule and a mixing chamber provided between the carpule and exit port. More specifically, the mixing chamber is downstream from the carpule and upstream from the exit port.

The mixing chamber can further include a turbulence-forming structure within the lumen of the mixing chamber to facilitate mixing of the compositions or solutions when delivered from their respective carpules or carpule chambers.

In addition, each stem of the dual-stemmed plunger can be a predetermined length, or can be adjusted to provide a certain length corresponding to an amount or volume of solution to be delivered from its engaged carpule. For example, a stem having a length of 1× centimeters will deliver one-half the amount or volume of a stem having a length of 2× centimeters. Each stem can be a calibrated, fixed length for predetermined volume delivery, or at least one stem length can be adjustable for determining volumes to be delivered. In a preferred embodiment, the dual-stem plunger comprises one stem of fixed length, and one stem of adjustable length. Adjustable-length stems are well-known in the art, and typically are fabricated as a threaded mechanism having calibrations corresponding to the adjusted length of the stem.

In any case, depressing or actuating the plunger causes the carpule cap to be depressed against the carpule-piercing means, whereby the carpule cap is pierced or punctured to allow delivery of the predetermined amount or volume of drug and second injectable fluid to the mixing chamber. The two solutions are thoroughly mixed in the mixing chamber before being administered through the exit port or nozzle used for injection of the mixed drug/buffer composition into the tissue of a patient in need of the mixed drug/buffer composition.

Turning now to the Figures, FIG. 1 is a top view of an embodiment of a syringe device 10 in accordance with the subject invention, illustrating the line of cross-section A-A, by which all other views are shown in FIGS. 2-6.

Figure 2:
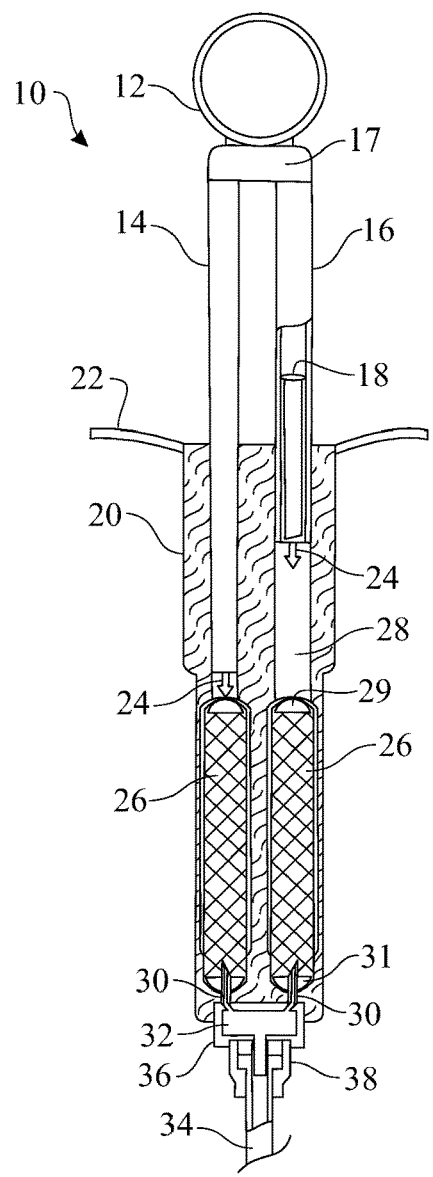
FIG. 2 is a cross-sectional side view of an embodiment of a syringe device in accordance with the subject invention, illustrating the components of the device, including a dual-stemmed plunger providing different volumes or amounts of each fluid from a single actuation, and shown in extended position, prior to actuation.

FIG. 2 is a partial cross-sectional side view of an embodiment of a syringe device 10 in accordance with the subject invention, illustrating components of the device. FIG. 2 illustrates an embodiment of a syringe of the invention in extended position, prior to or flowing actuation of the plunger and administration of the solution(s). Shown are: a plunger ring 12 connected to a single plunging actuator 17 comprising dual stems 14 and 16 extending therefrom.

Stem 14 is shown having a fixed, non-adjustable length. The other stem 16 (shown in partial cut-away view) comprises a stem-adjusting means 18 which provides for adjusting the length of the stem 16. For example a stem-length adjusting means can be a rod threaded on its outer surface such that it threadingly and matingly engages with an inner threaded surface of stem 16. The adjustable-length stem can provide for delivery of different or varying desired volumes or amounts of solution from actuation of the adjustable stem. For example, FIG. 1 shows stem 14 having a different length than stem 16, whereby stem 14 is longer and can deliver a greater amount of fluid than stem 16 when both are operated by a single actuation of the plunger.

The plunger stems 14 and 16 slidingly engage with the respective chambers 28 formed in the syringe barrel or body 20, and the stems are positioned superior to carpules 26, which contain the drug composition or diluent, buffer or other composition.

Preferably, the inferior end of each plunger stem comprises a penetrating means 24, e.g., a pointed or sharpened end integral with or affixed to, the stem for penetrating into the carpule plug. This carpule plug-penetrating means can facilitate, during actuation of the plunger, engagement of the stem with the carpule plug 29 provided in the superior end of the carpules 26. The material forming carpule plug 29 is partially, but preferably not completely, penetrated by the penetrating means 24 at the inferior end of plunger stems 14 and 16. Carpule plugs 29 are preferably dimensioned to have a thickness to be partially penetrated by the penetrating means, and a circumference which provides for slidingly engaging with the inner wall of the carpule in a leak-proof manner.

At their inferior end, carpules 26 comprise a cap 31, which can engage, and be completely pierced or punctured by carpule piercing means 30. In a preferred embodiment, the carpule-piercing means comprises a tube, preferably having a sharp, tapered or pointed end which can puncture through the end cap of the carpule when pressed against the cap.

The carpule piercing means is preferably tubular, having a lumen which communicates with the solution within the carpule, and with a mixing chamber 32, providing a conduit to deliver the solutions to the mixing chamber.

The mixing chamber 32 is in further communication with an exit port or nozzle 36, which can comprise a needle-securing nut 38 for removably engaging a hypodermic needle 34.

Figure 3:
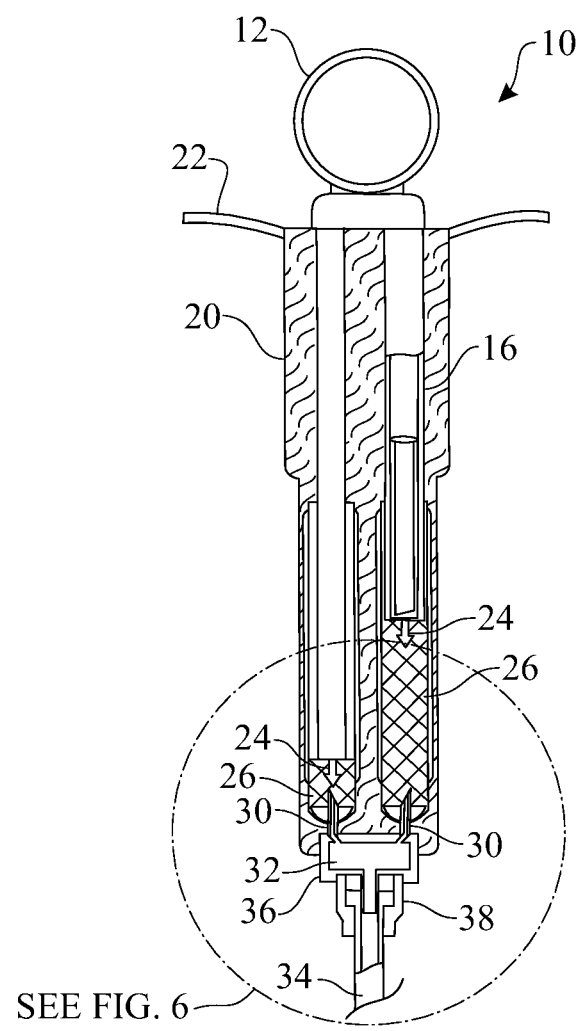
FIG. 3 is a cross-sectional side view of an embodiment of a syringe device in accordance with the subject invention, illustrating the components of the device, including a dual-stemmed plunger providing different volumes of each fluid from a single actuation, as shown in a depressed or actuated position; the circular broken line identifying the area detailed in FIG. 6.
Figure 6:
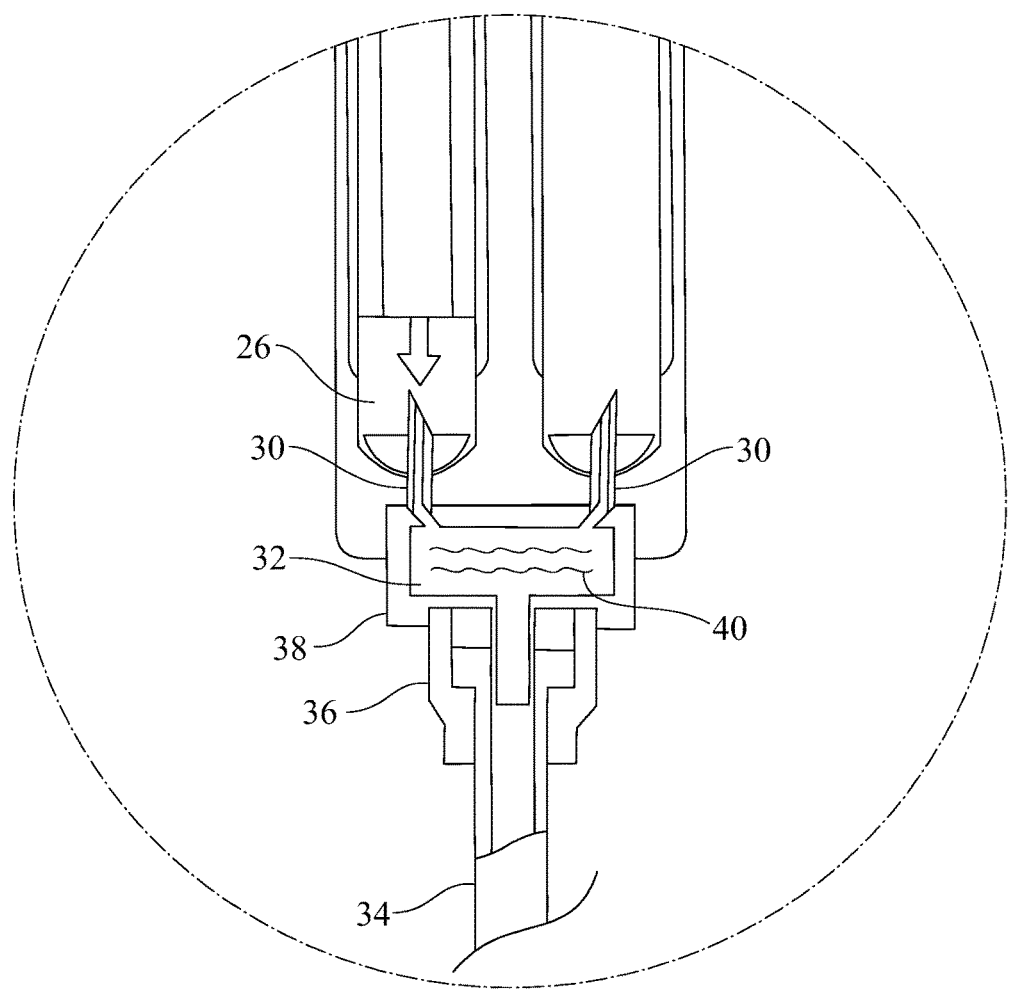
FIG. 6 is a cross-sectional side view of the inset (circular broken line) of FIG. 3.

FIG. 3 is a partial cross-sectional side view of an embodiment of a syringe device shown in FIG. 2, but shown in a depressed or actuated position; the circular broken line identifies an inset, which is the area detailed in FIG. 6 and the accompanying description.

Figure 4:
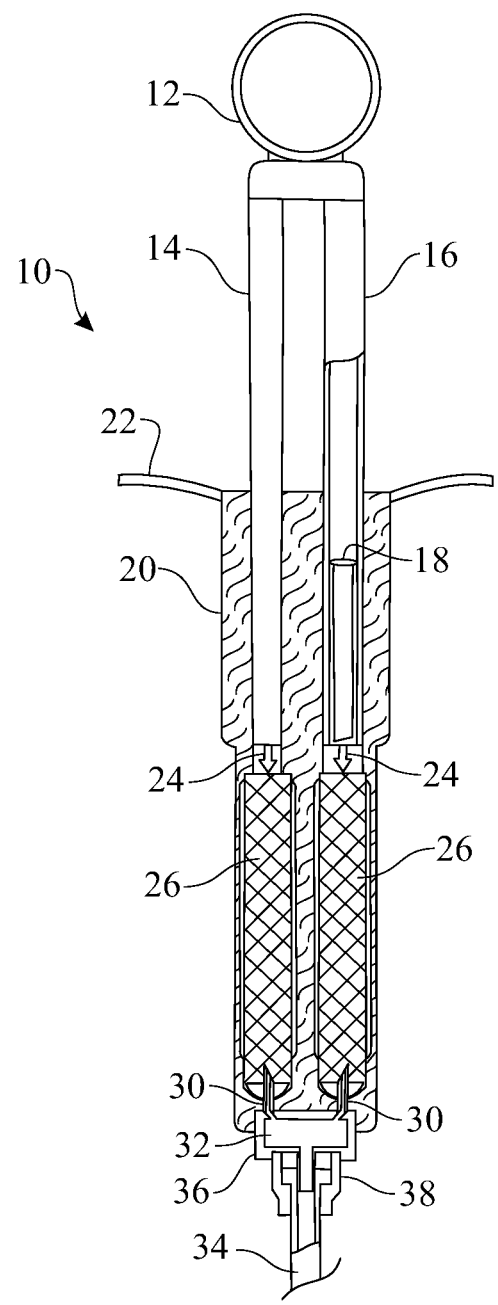
FIG. 4 is a cross-sectional side view of an embodiment of a syringe device in accordance with the subject invention, illustrating the components of the device, including a dual-stemmed plunger providing identical volumes or amounts of each fluid from a single actuation, and shown in extended position, prior to actuation.

FIG. 4 is a partial cross-sectional side view of an embodiment of a syringe device 10 in accordance with the subject invention, illustrating components of the device. FIG. 4 illustrates an embodiment of a syringe of the invention in extended position, prior to actuation of the plunger and administration of the solution(s). Shown are: a plunger ring 12 connected to a single plunging actuator comprising dual stems extending therefrom.

Stem 14 is shown having a fixed, non-adjustable length. The other stem 16 (shown in partial cut-away view) comprises a stem-adjusting means 18 which provides for adjusting the length of the stem within stem housing 16. For example a stem-length adjusting means can be a rod threaded on its outer surface such that it threadingly and matingly engages with an inner threaded surface of housing 16. The adjustable-length stem can provide for delivery of different or varying desired volumes or amounts of solution from actuation of the adjustable stem. As shown here, FIG. 4 illustrates the length of the adjustable-length stem 16 is set to be equal to the length of stem 14 in order to provide for delivery of a desired volume or amount of solution equal to the volume or amount delivered from the fixed-length stem, from a single actuation of the plunger.

The plunger stems 14 and 16 slidingly engage with the respective chambers 28 formed in the syringe barrel or body 20, and the stems are positioned superior to carpules 26, which contain the drug composition or diluent, buffer or other composition.

Preferably, the inferior end of each plunger stem comprises a penetrating means 24, e.g., a pointed or sharpened end integral with or affixed to, the stem for penetrating into the carpule plug. This carpule plug-penetrating means can facilitate, during actuation of the plunger, engagement of the stem with the carpule plug 29 provided in the superior end of the carpules 26. The material forming carpule plug 29 is partially, but preferably not completely, penetrated by the penetrating means 24 at the inferior end of plunger stems 14 and 16. Carpule plugs 29 are preferably dimensioned to have a thickness to be partially penetrated by the penetrating means, and a circumference which provides for slidingly engaging with the inner wall of the carpule in a leak-proof manner.

At their inferior end, carpules 26 comprise a cap 31, which can engage, and be completely pierced or punctured by carpule piercing means 30. In a preferred embodiment, the carpule-piercing means comprises a tube, preferably having a sharp, tapered or pointed end which can puncture through the end cap of the carpule when pressed against the cap.

The carpule piercing means is preferably tubular, having a lumen which communicates with the solution within the carpule, and with a mixing chamber 32, providing a conduit to deliver the solutions to the mixing chamber.

The mixing chamber 32 is in further communication with an exit port or nozzle 36, which can comprise a needle-securing nut 38 for removably engaging a hypodermic needle 34.

Figure 5:
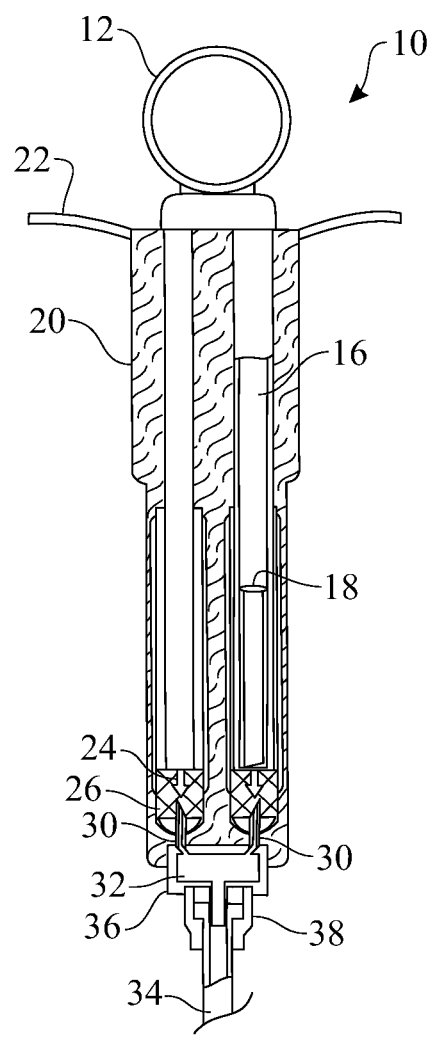
FIG. 5 is a cross-sectional side view of an embodiment of a syringe device in accordance with the subject invention, illustrating the components of the device, including a dual-stemmed plunger providing identical volumes of each fluid from a single actuation, as shown in a depressed or actuated position.

FIG. 5 is a partial cross-sectional side view of an embodiment of a syringe device shown in FIG. 4, but shown in a depressed or actuated position.

FIG. 6 is a cross-sectional side view of the inset (circular broken line) of FIG. 3. Specifically shown are the carpule 26, carpule-piercing means 30 having a tubular configuration, i.e., having an open lumen to provide for communication between the solution within the carpule and mixing chamber 32. The nozzle 38 formed at one end of the mixing chamber comprises a needle-securing nut 36 for securing a disposable hypodermic needle 34 thereto.

Further, in a preferred embodiment, the mixing chamber can comprise a turbulence-forming structure 40 to facilitate mixing of the two fluids entering the mixing chamber. A turbulence-forming structure is preferably an inert material, typically formed in an amorphous or convoluted shape such that laminar flow of the fluid contacting the structure is interrupted, thereby creating turbulence of flow of the fluid(s), which can facilitate mixing of two fluids within a chamber.

Figure 7:
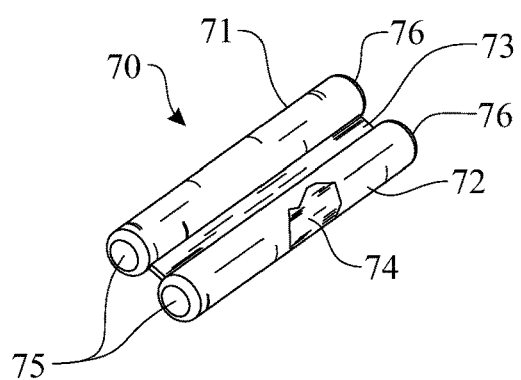
FIG. 7 shows a perspective cross-sectional view of an embodiment of a dual-chambered carpule according to the invention.

FIG. 7 shows a perspective, partially cross-sectional view of an embodiment of a dual-chambered carpule according to the invention. Specifically, FIG. 7 illustrates carpule 70 comprising two cylinders 71 and 72 for containing a medicament or diluent. Cylinders 71 and 72 are connected to one another by connecting means 73, which can be a connecting flange or can be an adhesive or other affixing material which holds the cylinders together in tandem. Each cylinder has a hollow core 74 for holding and containing therewithin a fluid for dispensing by the user of a syringe device according to the subject invention.

Each cylinder comprises a tubular structure having open ends which are closed by a puncturable carpule cap 75 at one end (preferably forming the inferior end), and further comprise a sliding plug 76 at the other end (superior end). The dual-chambered carpule can be any practical shape which provides containment of the drug and/or diluent, and fits within a double-barreled syringe of the invention.

The present invention provides advantages over prior devices in, at least the following ways:

it allows for mixing and dispensing local anesthetic and buffering solution from a single syringe using prefabricated carpules dispensed in a single actuating step;

the dispensing apparatus can provide a method of mixing buffered solution which provides a convenient and all-in-one step of producing a thoroughly and precise mixture of buffered anesthetic solution;

it does not require any activation step; therefore it is better suited for practicality and efficiency in a clinical setting.

it provides a method of mixing buffered local anesthetic solution which will obviate the necessity of any mixing steps prior to loading into a syringe for administration;

it provides a disposable needle assembly being inexpensive to manufacture, efficient in operation and readily attached and removed from the syringe body;

it provides a disposable double-barrel carpule which may be readily and easily inserted into a syringe body for use, and readily and easily removed therefrom after use;

it provides a disposable readily and easily inserted double-barrel carpule which is, in one of the barrels, prefilled with sodium bicarbonate solution and gas-tight headspace containing $CO_2$ gas which enables storage of sodium bicarbonate solution in an equilibrium state in a closed system readily available for mixing or dispensing; the other barrel prefilled with commercial local anesthetic solution;

it provides a syringe assembly with a mixing chamber which facilitates dispensing of buffered local anesthetic solution instantly prior to administering the solution into the intended target tissue;

it provides a syringe system for simultaneously transferring solutions in preset ratios and amounts from a double cartridge system into a mixing chamber;

it provides a syringe with an autoclavable (sterilizable) mixing chamber; it provides a syringe with a reusable mixing chamber;

it provides a syringe mixing chamber causing turbulence between the two solutions when the double plunger is axially actuated;

it provides a syringe assembly with a double-cartridge piercing connectors for providing fluid transfer paths from the double chamber cartridge into a common mixing chamber; and it provides a syringe double-carpule assembly having the same length and where the diameter of one carpule is smaller than the other (8:1 ratio).

In use, a syringe of the subject invention is manipulated and utilized in a manner similar to a conventional carpule-holding syringe, except that two carpules are loaded within the syringe barrel prior to administration of a medicament. Specifically, the method comprises the steps of:

a) providing a syringe having a double-chambered barrel capable of receiving two carpules, a dual-stemmed plunger, and mixing chamber, as described herein;

b) loading at least one carpule containing a drug or drug solution into a first chamber of a double-chambered syringe barrel or body;

c) loading a second carpule containing a diluent, buffer, or second drug solution into a second chamber of a double-chambered syringe barrel or body;

d) checking calibration for accurate and precise amounts or volumes of solution from each respective carpule, and optionally adjusting said calibration as desired; and e) actuating, in a single step, the plunger to deliver the solutions from each carpule into the mixing chamber, and administer the mixed solutions into a target tissue.

The method can further include removing the expended carpules from the syringe barrel and repeating the above steps a) through e) as needed.

It is contemplated that the invention provides a significant role in ease-of-use and efficiency in administering local anesthetic buffered solution in a pH control fashion. The present invention provides optimal dosing control of freshly buffered local anesthetic solution at the fingertips of medical practitioners.

The invention claimed is:

1. A syringe for administering a mixture of an injectable anesthetic drug composition and a diluent for the injectable anesthetic drug composition, said syringe comprising:

a hollow syringe body bounding a syringe chamber, said syringe body being adapted for receiving an at least one carpule within the syringe chamber;

the syringe having an exit port at a proximal end of the syringe;

the at least one carpule comprising either a dual-chambered carpule or two single-chambered carpules, wherein one carpule chamber of the dual-chambered carpule or two single-chambered carpules contains the injectable anesthetic drug composition, and an other carpule chamber of the dual-chambered carpule or two single-chambered carpules contains the diluent;

a dual-stemmed syringe plunger, wherein one stem of the dual-stemmed syringe plunger has a fixed length, and an other stem of the dual-stemmed syringe plunger has an adjustable length, each stem of the dual-stemmed syringe plunger having a superior end and an inferior end, wherein the inferior end of each stem slidingly engages with a sliding plug at a superior end of the dual-chambered carpule or two single-chambered carpules, said dual-chambered carpule or two single-chambered carpules further comprising a sealed or capped inferior end;

a carpule-piercing conduit for engaging with and piercing or puncturing the sealed or capped inferior end when pressure is applied by the dual-stemmed syringe plunger, said carpule piercing conduit being superior to and in communication with a mixing chamber;

the mixing chamber being removable from the syringe body and located between the dual-chambered carpule or two single-chambered carpules and the exit port, the mixing chamber for receiving and adequately mixing the injectable anesthetic drug composition and the diluent dispensed from the dual-chambered carpule or two single-chambered carpules, said mixing chamber having a turbulence-forming structure comprising an inert material formed in an amorphous or convoluted shape and being disposed within a lumen of the mixing chamber such that a flow of the injectable drug composition and the diluent contacting the turbulence-forming structure is interrupted, thereby creating turbulence and mixing of the injectable anesthetic drug composition and the diluent within the mixing chamber prior to administration of the mixture;

the exit port at the proximal end of the syringe for dispensing the mixture from the mixing chamber, said exit port configured to receive a disposable needle for injection of the mixture into a patient; and whereby, depressing or actuating the dual-stemmed syringe plunger causes piercing of the sealed or capped inferior end of the dual-chambered carpule or two-single chambered carpules to deliver a predetermined amount or volume of the injectable anesthetic drug composition and the diluent into the mixing chamber for mixing and through the exit port at the proximal end of the syringe.

2. The syringe of claim 1, wherein the at least one carpule is the dual-chambered carpule, said dual-chambered carpule comprising two cylinders, each cylinder having a hollow core for containing either the injectable anesthetic drug composition or the diluent, wherein the two cylinders are affixed together in tandem for use with the syringe.

* * * * *